United States Patent [19]

Harada et al.

[11] Patent Number: 4,775,656
[45] Date of Patent: Oct. 4, 1988

[54] RECORDING MATERIAL CONTAINING LEUCO DYE

[75] Inventors: Toru Harada; Toshiyuki Watanabe, both of Kanagawa, Japan

[73] Assignee: Fuji Photo Film Co., Ltd., Kanagawa, Japan

[21] Appl. No.: 115,064

[22] Filed: Oct. 30, 1987

[30] Foreign Application Priority Data

Oct. 30, 1986 [JP] Japan .................................. 61-259965

[51] Int. Cl.$^4$ ..................... B41M 5/16; C07D 407/04; C07D 493/10
[52] U.S. Cl. .................................. 503/221; 549/224; 430/138; 430/281; 430/541
[58] Field of Search ....................... 503/221; 549/224; 430/138, 281, 541

[56] References Cited

U.S. PATENT DOCUMENTS

| | | | |
|---|---|---|---|
| 4,156,682 | 5/1979 | Hotta et al. | 549/224 |
| 4,624,910 | 11/1986 | Takeda | 430/203 |
| 4,629,676 | 12/1986 | Hayakawa et al. | 430/203 |
| 4,649,098 | 3/1987 | Takeda | 430/270 |

FOREIGN PATENT DOCUMENTS 24646  4/1970  Japan .................................. 503/221

*Primary Examiner*—Paul R. Michl
*Assistant Examiner*—Patrick A. Doody
*Attorney, Agent, or Firm*—Sughrue, Mion, Zinn, Macpeak & Seas

[57] ABSTRACT

A recording material comprises a layer containing a leuco dye provided on a support, characterized in that the leuco dye has the formula (I):

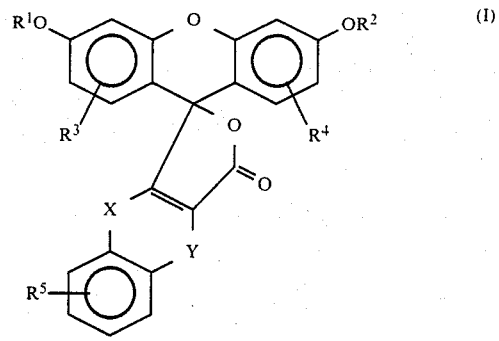

in which one of X and Y is a single bond and the other is sulfur atom; each of $R_1$ and $R^2$ independently is an alkyl group, a cycloalkyl group or an aralkyl group; each of $R^3$ and $R^4$ independently is hydrogen, a halogen atom, an alkyl group, an alkoxy group, a cycloalkyl group, an aralkyl group or an aryloxy group; $R^5$ is hydrogen, a halogen atom, an alkyl group, an alkoxy group, nitro or amino; and each of $R^1$, $R^2$, $R^3$, $R^4$ and $R^5$ may have one or more substituent groups.

9 Claims, No Drawings

RECORDING MATERIAL CONTAINING LEUCO DYE

BACKGROUND OF THE INVENTION

1. Field of the Invention

This invention relates to a recording material such as a light-sensitive mateiral, a heat-sensitive material and a pressure-sensitive material, and more particularly to a recording material containing a leuco dye.

2. Description of Prior Art

In various recording materials including light-sensitive, heat-sensitive and pressure-sensitive materials, a leuco dye is frequently used as a color image forming substance. In leuco dye, which is also referred to as a redox dye, develops a color on contact with an acid color developer.

The leuco dye is generally contained in microcapsules which are dispersed in a recording material. In an image forming process, the microcapsules are broken by external energy such as pressure and/or heat so that the dye comes into contact with the acid color developer which is arranged outside of the microcapsules in the recording material.

Conventional leuco dyes which develop yellow are described in Japanese Patent Publication Nos. 45(1970)-4698, 50(1975)-24646, 51(1976)-27169 and 53(1978)-9127 and Japanese Patent Provisional Publication No. 49(1974)-4480. It is described in these Publications that most of the leuco dyes are advantageously used in a pressure-sensitive material. In addition to the pressure-sensitive material, leuco dyes are also employed in other recording materials, such as a light-sensitive mateiral and a heat-sensitive material.

Examples of the light-sensitive material include a light-sensitive material comprising a light-sensitive layer containing silver halide, a reducing agent and a polymerizable compound provided on a support as well as conventional silver salt photo-sensitive materials. The light-sensitive material containing silver halide, a reducing agent and a polymerizable compound is described in U.S. Pat. No. 4,629,676 and Japanese Patent Provisional Publication Nos. 61(1986)-183640, 61(1986)-188535, 61(1986)-228441, 61(1986)-243449, 61(1986)-260241, 61(1986)-275742 and 61(1986)-278849. Further, the light-sensitive material containing a leuco dye which developes yellow is described in Japanese Patent Application Nos. 61(1986)-133091 and 61(1986)-133092.

SUMMARY OF THE INVENTION

An object of the present invention to provide a recording material which gives a yellow color image improved in the color density and the light fastness.

Another object of the invention is to provide a recording material which is advantageously used as a light-sensitive material containing silver halide, a reducing agent and a polymerizable compound.

There is provided by the present invention a recording material comprising a layer containing a leuco dye provided on a support, wherein the leuco dye is a novel leuco dye having the formula (I):

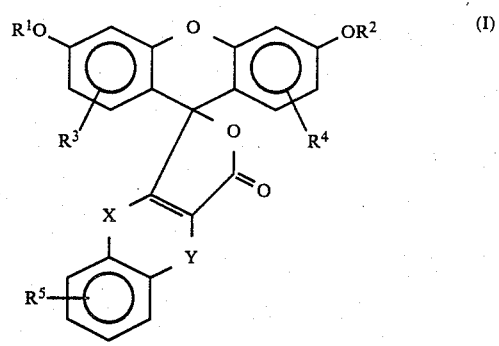

in which one of X and Y is a single bond and the other is sulfur; each of $R^1$ and $R^2$ independently is a monovalent group selected from the group consisting of an alkyl group, a cycloalkyl group and an aralkyl group; each of $R^3$ and $R^4$ independently is a monovalent group selected from the group consisting of hydrogen, a halogen atom, an alkyl group, an alkoxy group, a cycloalkyl group, an aralkyl group and an aryloxy group; $R^5$ is a monovalent group selected from the group consisting of hydrogen, a halogen atom, an alkyl group, an alkoxy group, nitro grop and amino; and each of $R^1$, $R^2$, $R^3$, $R^4$ and $R^5$ may hve one or more substituent groups.

The recording material of the invention is advantageously used as a light-sensitive material where the recording material comprises a light-sensitive layer containing silver halide, a reducing agent, a polymerizable compound and the leuco dye provided on a support.

The present inventors have found that the novel leuco dye having the formula (I) is improved in the light fastness of the developed color. Therefore, the leuco dye can be used as an excellent color image forming substance (yellow color image forming substance) contained in a recording material.

The present inventors have further found that the leuco dye is much improved in the color developing rate and the density of the developed color. These improvements are especially advantageous to the light-sensitive material containing silver halide, a reducing agent, a polymerizable compound because the efficiency of leuco dye is relatively low in the image formation employing the light-sensitive material, since the leuco dye is usually dissolved in the polymerizable compound in the light-sensitive material.

DETAILED DESCRIPTION OF THE INVENTION

The leuco dyes employed in the present invention has the formula (I-a) or (I-b).

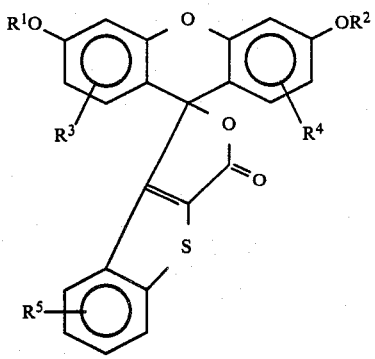

(I-a)

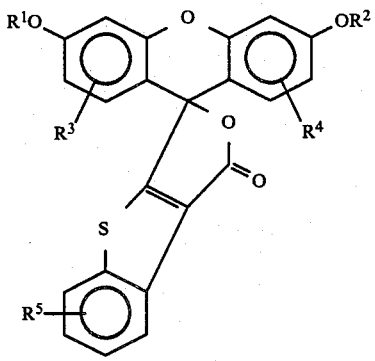

(I-b)

In the formula (I-a) or (I-b), each of $R^1$ and $R^2$ independently is a monovalent group selected from the group consisting of an alkyl group, a cycloalkyl group and an aralkyl group; each of $R^3$ and $R^4$ independently is a monovalent group selected from the group consisting of hydrogen, a halogen atom, an alkyl group, an alkoxy group, a cycloalkyl group, an aralkyl group and an aryloxy group; $R^5$ is a monovalent group selected from the group consisting of hydrogen, a halogen atom, an alkyl group, an alkoxy group, nitro and amino; and each of $R^1$, $R^2$, $R^3$, $R^4$ and $R^5$ may have one or more substituent groups.

The alkyl group represented by $R^1$ to $R^5$ preferably has 1 to 22 carbon atoms, and more preferably has 1 to 12 carbon atoms. The alkyl group may be a straight chain or a branched chain and may have one or more substituent groups such as a halogen atom, cyano, an alkoxy group and hydroxyl.

Examples of the cycloalkyl groups represented by $R^1$ to $R^4$ include cyclopentyl, cycloheptyl and cyclooctyl.

Examples of the aralkyl groups represented by $R^1$ or $R^4$ include benzyl and phenethyl. The aryl moiety of the aralkyl group may have one or more substituent groups such as a halogen atom, a lower alkyl group (having 1 to 4 carbon atoms), a lower alkoxy group (having 1 to 4 carbon atoms) and nitro.

The halogen atom represented by $R^3$, $R^4$ and $R^5$ preferably is chlorine or bromine.

The alkyl moiety of the alkoxy group preferably has 1 to 12 carbon atoms. The alkoxy group may have one or more substituent groups such as cyano, a halogen atom, an alkoxy group and hydroxyl.

The aryl moiety of the aryloxy group is preferably phenyl. The aryloxy group may have one or more substituent groups such as a halogen atom, a lower alkyl group (having 1 to 4 carbon atoms), a lower alkoxy group (having 1 to 4 carbon atoms) and nitro.

The amino represented by $R^5$ may have one or more substituent groups such as an alkyl group, a cycloalkyl group, an aralkyl group and an aryl group. The alkyl group preferably has 1 to 22 carbon atoms, and more preferably has 1 to 12 carbon atoms. The alkyl group may be a straight chain or a branched chain and may further have one or more substituent groups such as a halogen atom, cyano, an alkoxy group and hydroxyl. Examples of the cycloalkyl groups include cyclopentyl, cycloheptyl and cyclooctyl. Examples of the aralkyl groups include benzyl and phenethyl. The aryl moiety of the aralkyl group may further have one or more substituent groups such as a halogen atom, a lower alkyl group (having 1 to 4 carbon atoms), a lower alkoxy group (having 1 to 4 carbon atoms) and nitro. Example of the aryl group is phenyl. The aryl group may further have one or more substituent groups such as a halogen atom, a lower alkyl group (having 1 to 4 carbon atoms), a lower alkoxy group (having 1 to 4 carbon atoms) and nitro.

Examples of the leuco dyes which are preferably used in the invention are described hereinafter. The following examples are the compounds having the formula (I-a). However, isomers of the examples having the formula (I-b) are also available in the invention.

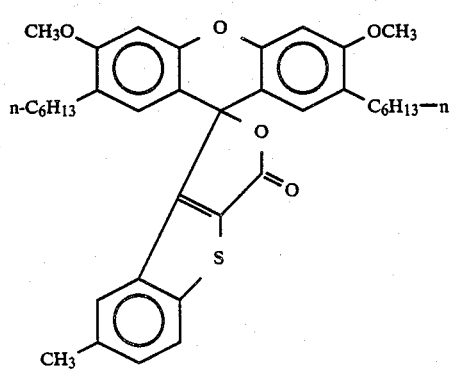

(1)

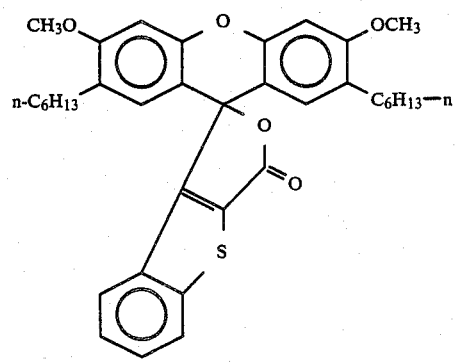

(2)

-continued
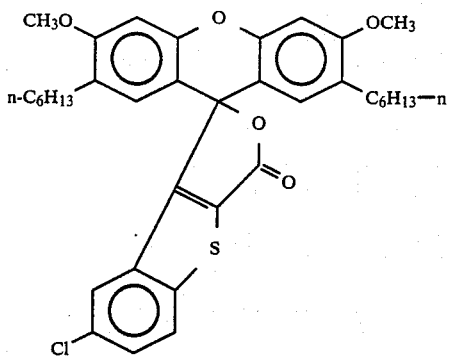   (3)
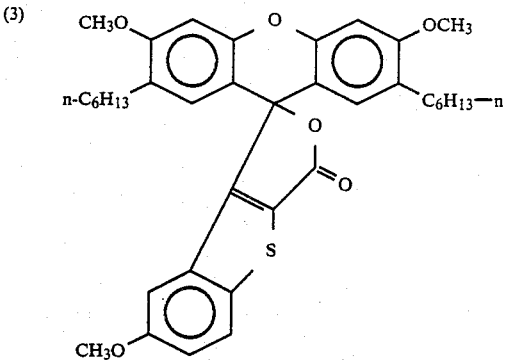   (4)
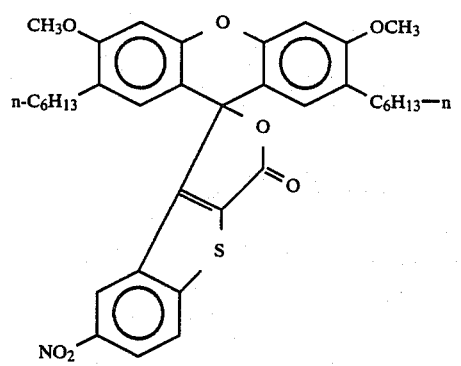   (5)
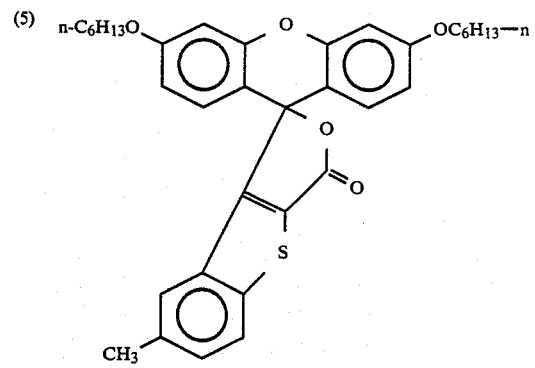   (6)
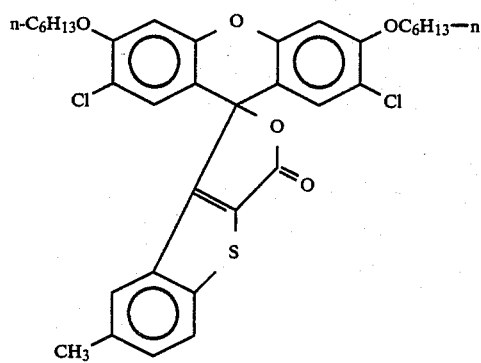   (7)
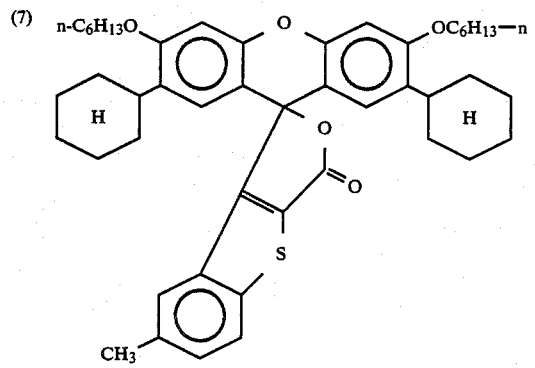   (8)
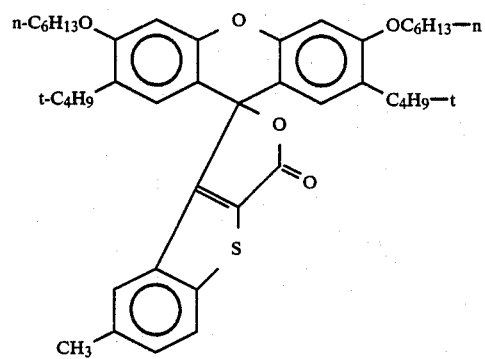   (9)
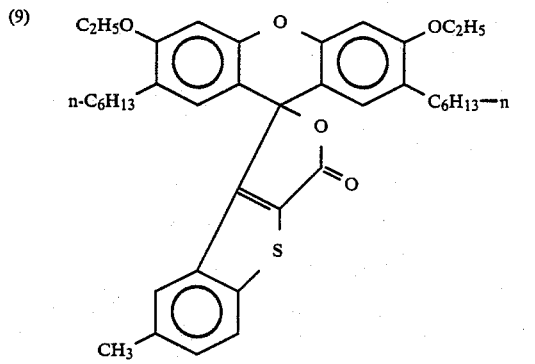   (10)

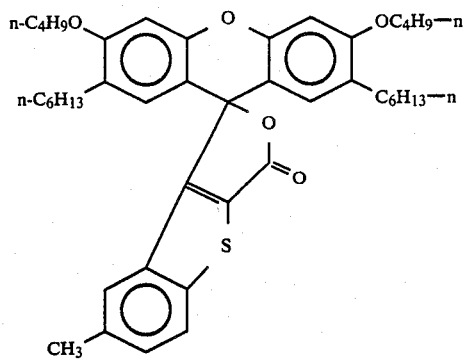
(11)

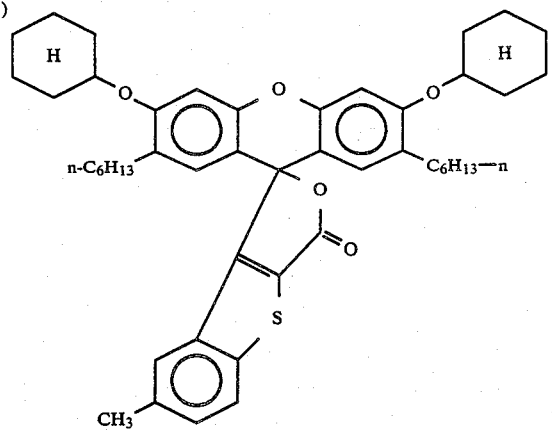
(12)

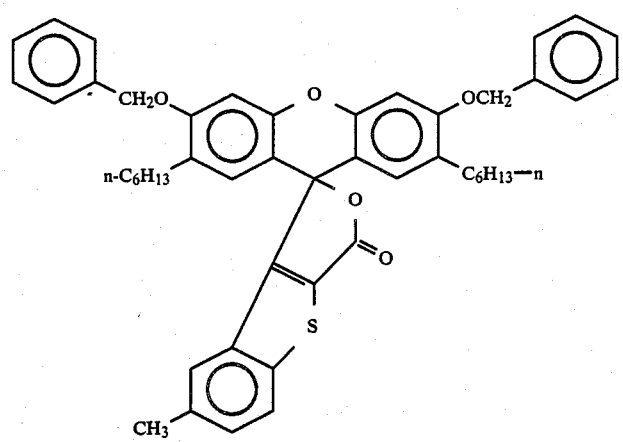
(13)

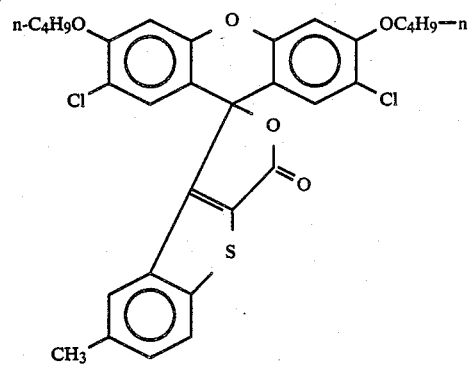
(14)

The leuco dyes used in the present invention can be easily synthesized according to the following reaction formulas. The following reaction formulas show a process for synthesis of a leuco dye in which $R^1$ and $R^2$ in the formula (I-a) or (I-b) are identical and $R^3$ and $R^4$ in the formula (I-a) or (I-b) are also identical. The synthesized isomers having a formula (I-a) or (I-b) can be separated from each other using column chromatography.

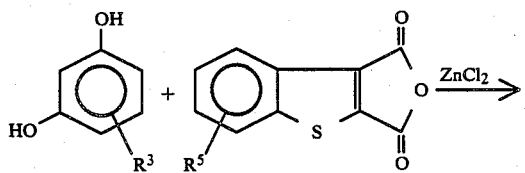

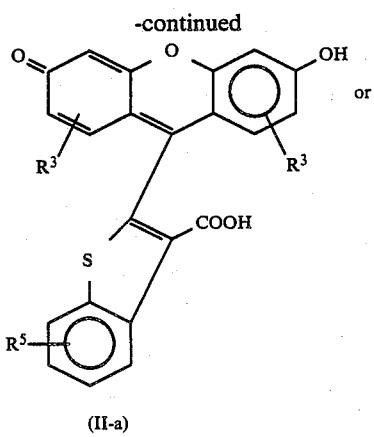

(II-a)

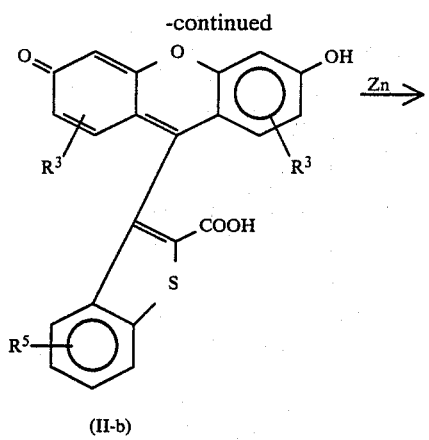

(II-b)

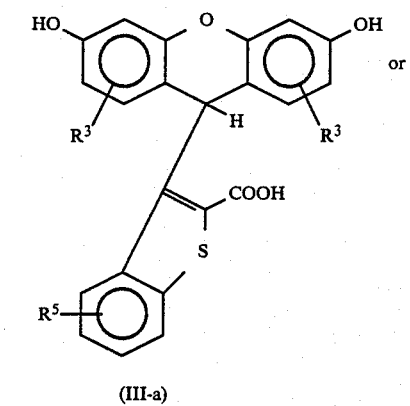

(III-a)

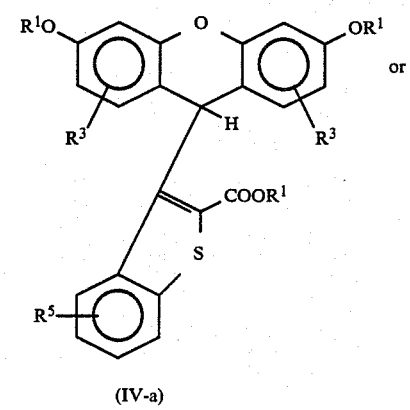

(III-b)

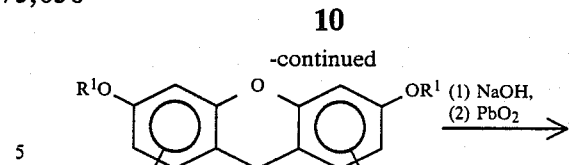

(IV-a)

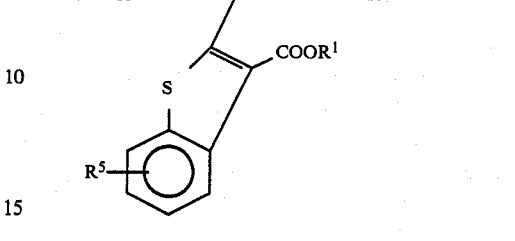

(IV-b)

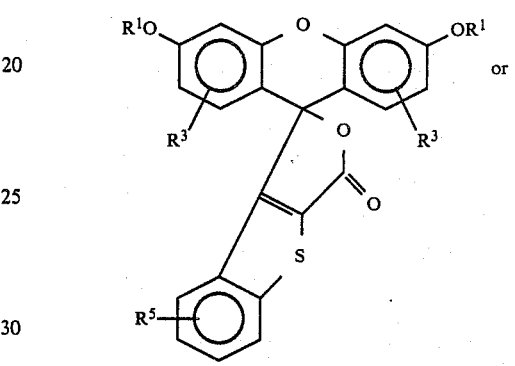

(I-a)

(I-b)

An example for synthesizing the leuco dye (1) will be described below on the basis of the above-mentioned reaction scheme.

SYNTHESIS EXAMPLE 1

Synthesis of lueco dye (1)

In a three-necked flask were placed 20 g of 5-methyl-benzothiophene-2,3-dicarboxylic anhydride, 34 g of hexylresorcinol and 23.5 g of zinc chloride, and the mixture was stirred at 130° C. for 4 hours. The reaction mixture was extracted with ethyl acetate and water. The ethyl acetate layer was separated and allowed to stand to obtain a crystalline precipitate, which was a compound of the formula (II-a). The yield was 9.9 g.

To 4 g of the obtained product were added 40 ml of acetic acid and 6.6 g of zinc, and the mixture was stirred at 70° C. for 2 hours. The mixture was filtered, and the filtrate was poured into water to obtain a crystalline precipitate. The precipitate was then filtered to obtain a compound of the formula (III-a). The yield was 3.8 g.

To 3.8 g of the obtained product were added 7.2 g of methyl p-toluenesulfonate, 5.4 g of potassium carbonate and 10 ml of N,N-dimethylacetamide, and the mixture was stirred at 90° C. for 5 hours. The reaction mixture was poured into aqueous hydrochloric acid, and the mixture was extracted with ethyl acetate. The extract was then concentrated under reduced pressure and filtered to obtain a crystalline precipitate, which is a compound of the formula (IV-a). The yield was 2.9 g.

To 2.9 g of the obtained product were added 13 ml of ethyl alcohol and 0.9 g of sodium hydroxide in 1.4 ml of water, and the mixture was refluxed for 2 hours. The reaction mixture was poured into aqueous hydrochloric acid and the mixture was extracted with 80 ml of ethyl acetate. To the extract was added 15 g of lead dioxide and the resulting mixture was refluxed for 2 hours. The mixture was concentrated under reduced pressure and recrystallized from a solvent (ethyl acetate/n-hexan=5 ml/15 ml) to obtain a leuco dye (1). The yield was 2.0 g, m.p. 141°–142° C.

The leuco dye (6) and the leuco dye (14) were synthesized in a similar manner to that of Synthesis Example 1. The melting point of the leuco dye (6) was 75°–80° C., and that of the leuco dye (14) was 210°–212° C.

The other leuco dyes can be prepared by procedures similar to that of Synthesis Example 1.

These leuco dyes can be used singly or in combination. For example, a leuco dye having the formula (I-a) can be used in combination with a leuco dye having the formula (I-b). Other leuco dyes can be used in combination with the leuco dye of the invention to obtain various kinds of color images, whether the other leuco dye has the same hue as that of the leuco dye of the invention or not.

The leuco dye contained in the recording material of the invention develops a color on contact with an acid color developer. In the case that the acid color developer is also contained in the recording material of the invention, the developer is arranged out of contact with the leuco dye. For instance, the leuco dye is contained in microcapsules and the acid color developer is arranged outside of the microcapsules in the recording material. Alternatively, the leuco dye and the developer can be contained in separated layers respectively. In the image forming process, the recording material is pressed or heated so that the leuco dye comes into contact with the acid color developer. In another embodiment, the acid color developer can be contained in a material different from the recording material of the invention containing the leuco dye. In the image forming process, the recording material is pressed or heated on the material containing the developer so that the leuco dye comes into contact with the developer. In these embodiment, the acid color developer can be containined in microcapsules which are different from those containing the leuco dye.

In the case that the recording material of the invention is used as a light-sensitive material or a pressure-sensitive material, the leuco dye is preferably contained in microcapsules. More preferably, the acid color developer is contained in another layer which is different from the layer of the microcapsules. The layer containing the developer can be provided on a material (an image-receiving material or a developer sheet) different from the recording material of the invention. In the case that the microcapsules are employed as mentioned above, the obtained color image can be improved in the sensitivity and sharpness.

In the image forming process, the leuco dye preferably comes into contact with the acid color developer at an elevated temperature. The color forming reaction can be greatly accelerated by heating the leuco dye and the developer. Heating temperature for the reaction usually ranges from 50° C. to 200° C., and preferably from 50° C. to 150° C. The heating time is usually from 1 second to 1 minute, and preferably from 1 second to 10 seconds.

Examples of the acid color developers include an acid clay developer (e.g., China clay), phenol-formaldehyde resins (e.g., p-phenylphenol-formaldehyde resin), metal salts of salicyclic acids (e.g., zinc 3,5-di-α-methylbenzyl salicylate), phenol-salicylic acid-formaldehyde resin (e.g., p-octylphenol-zinc salicylate-formaldehyde resin), zinc rhodanide and zinc xanthate.

Among them, the metal salts of the salicylic acids are preferred, and zinc salicylates are most preferred. It has been found that the reaction of the color formation of the leuco compound proceeds rapidly and effectively in the presence of zinc salicylates. The metal salts of the salicylates are described in more detail in Japanese Patent Publication No. 52(1977)-1327. The oil-soluble color developers containing zinc salicylates are described in U.S. Pat. Nos. 3,864,146 and 4,046,941.

The acid color developer is preferably used in an amount of from 50 to 1,000 weight % based on the amount of the leuco dye, and more preferably from 100 to 1,000 weight %.

The leuco dye of the present invention can be used in any of light-sensitive, pressure-sensitive and heat-sensitive materials. However, the leuco dye is advantageously used as a color image forming substance of a light-sensitive material containing silver halide, a reducing agent and a polymerizable compound. Therefore, the recording material of the invention is preferably used as the light-sensitive material.

The light-sensitive material comprising a light-sensitive layer containing silver halide, a reducing agent, a polymerizable compound and the leuco dye provided on a support is described below. Thus composed material is referred hereinafter to as "light-sensitive material".

The leuco dye in the light-sensitive layer of the light-sensitive material is preferably contained in an amount of from 0.5 to 50 weight % based on the amount of the polymerizable compound, and more preferably from 2 to 20 weight %.

There is no specific limitation with respect to silver halide contained in the light-sensitive layer of the light-sensitive material. Examples of the silver halides include as silver chloride, silver bromide, silver iodide, silver chlorobromide, silver chloroiodide, silver iodobromide, and silver chloroiodobromide in the form of grains.

The halogen composition of individual grains may be homogeneous or heterogeneous. The heterogeneous grains having a multilayered structure in which the halogen composition varies from the core to the outer shell (see Japanese Patent Provisional Publication Nos. 57(1982)-154232, 58(1983)-108533, 59(1984)-48755 and 59(1984)-52237, U.S. Pat. No. 4,433,048, and European Pat. No. 100,984) can be employed. A silver halide grain having a core/shell structure in which the silver iodide content in the shell is higher than that in the core can be also employed.

There is no specific limitation on the crystal habit of silver halide grains. For example, a tubular grain having an aspect ratio of not less than 3 can be used.

Two or more kinds of silver halide grains which differ in halogen composition, crystal habit, grain size, and/or other features from each other can be used in combination.

There is no specific limitation on grain size distribution of silver halide grains. For example, the silver halide grains having such a grain size distribution that the coefficient of the variation is not more than 20% can be employed.

The silver halide grains ordinarily have a mean size of 0.001 to 5 μm, more preferably 0.001 to 2 μm.

The total silver content (including silver halide and an organic silver salt which is one of optional components) in the light-sensitive layer preferably is in the range of from 0.1 mg/m² to 10 g/m². The silver content of the silver halide in the light-sensitive layer preferably is not more than 0.1 g/m², more preferably in the range of from 1 mg to 90 mg/m².

The reducing agent employed in the light-sensitive material has a function of reducing the silver halide and/or a function of accelerating or restraining a polymerization of the polymerizable compound. Examples of the reducing agents having these functions include various compounds, such as hydroquinones, catechols, p-aminophenols, p-phenylenediamines, 3-pyrazolidones, 3-aminopyrazoles, 4-amino-5-pyrazolones, 5-aminouracils, 4,5-dihydroxy-6-aminopyrimidines, reductones, aminoreductones, o- or p-sulfonamidophenols, o- or p-sulfonamidonaphthols, 2-sulfonamidoindanones, 4-sulfonamido-5-pyrazolones, 3-sulfonamidoindoles, sulfonamidopyrazolobenzimidazoles, sulfonamidopyrazolotriazoles, α-sulfonamidoketones, hydrazines, etc. Depending on the nature or amount of the reducing agent, the polymerizable compound within either the area where a latent image of the silver halide has been formed or the area where a latent image of the silver halide has not been formed can be polymerized. In the developing system in which the polymerizable compound within the area where the latent image has not been formed is polymerized, 1-phenyl-3-pyrazolidone is preferably employed as the reducing agent.

The light-sensitive materials employing the reducing agent having these functions (including compounds referred to as developing agent, hydrazine derivative or precursor of reducing agent) are described in Japanese Patent Provisional Publication Nos. 61(1986)-183640, 61(1986)-188535 and 61(1986)-228441. These reducing agents are also described in T. James, "The Theory of the Photographic Process", 4th edition, pp. 291-334 (1977), Research Disclosure No. 17029, pp. 9-15 (June 1978), and Research Disclosure No. 17643, pp. 22-31 (December 1978). The reducing agents described in the these publications can be employed in the light-sensitive material of the present invention. Thus, "the reducing agent(s)" in the present specification means to include all of the reducing agents described in the above mentioned publications and applications.

These reducing agents can be used singly or in combination. In the case that two or more reducing agents are used in combination, certain interactions between these reducing agents may be expected. One of the interactions is for acceleration of reduction of silver halide (and/or an organic silver salt) through so-called superadditivity. Other interaction is for a chain reaction in which an oxidized state of one reducing agent formed by a reduction of silver halide (and/or organic silver salt) induces or inhibits the polymerization of the polymerizable compound via oxidation-reduction reaction with other reducing agent. Both interactions may occur simultaneously. Thus, it is difficult to determine which of the interactions has occurred in practical use.

Examples of these reducing agents include pentadecylhydroquinone, 5-t-butylcatechol, p-(N,N-diethylamino)phenol, 1-phenyl-4-methyl-4-hydroxymethyl-3-pyrazolidone, 1-phenyl-4-methyl-4-heptadecylcarbonyloxymethyl-5-pyrazolidone, 2-phenylsulfonylamino-4-hexadecyloxy-5-t-octylphenol, 2-phenylsulfonylamino-4-t-butyl-5-hexadecyloxyphenol, 2-(N-butylcarbamoyl)-4-phenylsulfonylaminonaphtol, 2-(N-methyl-N-octadecylcarbamoyl)-4-sulfonylaminonaphthol, 1-acetyl-2-phenylhydrazine, 1-acetyl-2-(p- or o-aminophenyl)hydrazine, 1-formyl-2-(p- or o-aminophenyl)hydrazine, 1-acetyl-2-(p- or o-methoxyphenyl)hydrazine, 1-lauroyl-2-(p- or o-aminophenyl)hydrazine, 1-trityl-2-(2,6-dichloro-4-cyanophenyl)hydrazine, 1-trityl-2-phenylhydrazine, 1-phenyl-2-(2,4,6-trichlorophenyl)hydrazine, 1-{2-(2,5-di-tert-pentylphenoxy)butyloyl}-2-(p- or o-aminophenyl)hydrazine, 1-{2-(2,5-di-t-pentylphenoxy)butyloyl}-2-(p- or o-aminophenyl)hydrazine pentadecylfluorocapyrlate salt, 3-indazolinone, 1-(3,5-dichlorobenzoyl)-2-phenylhydrazine, 1-trityl-2-[{(2-N-butyl-N-octylsulfamoyl)-4-methanesulfonyl}phenyl]hydrazine, 1-{4-(2,5-di-tert-pentylphenoxy)butyloyl}-2-(p- or o-methoxyphenyl)hydrazine, 1-(methoxycarbonylbenzohydryl)-2-phenylhydrazine, 1-formyl-2-[4-{2-(2,4-di-tert-pentylphenoxy)butylamide}phenyl]hydrazine, 1-acetyl-2-[4-{2-(2,4-di-tert-pentylphenoxy)butylamido}phenyl]hydrazine, 1-trityl-2-[{2,6-dichloro-4-(N,N-di-2-ethylhexyl)carbamoyl}phenyl]hydrazine, 1-(methoxycarbonylbenzohydryl)-2-(2,4-dichlorophenyl)hydrazine, 1-trityl-2-[{2-(N-ethyl-N-octylsulfamoyl)-4-methanesulfonyl}phenyl]hydrazine, 1-benzoyl-2-tritylhydrazine, 1-(4-butoxybenzoyl)-2-tritylhydrazine, 1-(2,4-dimethoxybenzoyl)-2-tritylhydrazine, 1-(4-dibutylcarbamoylbenzoyl)-2-tritylhydrazine and 1-(1-naphthoyl)-2-tritylhydrazine.

The amount of the reducing agent in the light-sensitive layer preferably ranges from 0.1 to 1,500 mole % based on the amount of silver (contained in the above-mentioned silver halide and an organic silver salt).

There is no specific limitation with respect to the polymerizable compound, and any known polymerizable compounds including monomers, oligomers and polymers can be contained in the light-sensitive layer. In the case that heat development (i.e., thermal development) is utilized for developing the light-sensitive material, the polymerizable compounds having a relatively higher boiling point (e.g., 80° C. or higher) that are hardly evaporated upon heating are preferably employed. In the case that the light-sensitive layer contains a color image forming substance, the polymerizable compounds are preferably cross-linkable compounds having plural polymerizable groups in the molecule, because such cross-linkable compounds favorably serve for fixing the leuco dyes in the course of polymerization hardening of the polymerizable compounds.

The polymerizable compound employable for the light-sensitive material are described in the above-mentioned and later-mentioned publications concerning the light-sensitive material.

Preferred polymerizable compounds employable for the light-sensitive material are compounds which are polymerizable through addition reaction or ring-opening reaction. Preferred examples of the compounds being polymerizable through addition reaction include compounds having an ethylenic unsaturated group. Preferred examples of the compounds being polymerizable through ring-opening reaction include the compounds having an epoxy group. Among them, the compounds having an ethylenic unsaturated group are preferred.

Examples of compounds having an ethylenic unsaturated group include acrylic acid, salts of acrylic acid, acrylic esters, acrylamides, methacrylic acid, salts of methacrylic acid, methacrylic esters, methacrylamide, maleic anhydride, maleic esters, itaconic esters, styrene, styrene derivatives, vinyl ethers, vinyl esters, N-vinyl heterocyclic compounds, allyl ethers, allyl esters, and compounds carrying a group or groups corresponding to one or more of these compounds.

Concrete examples of the acrylic esters include n-butyl acrylate, cyclohexyl acrylate, 2-ethylhexyl acrylate, benzyl acrylate, furfuryl acrylate, ethoxyethoxy acrylate, dicyclohexyloxyethyl acrylate, nonylphenyloxyethyl acrylate, hexanediol diacrylate, butanediol diacrylate, neopentylglycol diacrylate, trimethylolpropane triacrylate, pentaerythritol tetraacrylate, dipentaerythritol pentaacrylate, diacrylate of polyoxyethylenated bisphenol A, polyacrylate of hydroxypolyether, polyester acrylate, and polyurethane acrylate.

Concrete examples of the methacrylic esters include methyl methacrylate, butyl methacrylate, ethylene glycol dimethacrylate, butanediol dimethacrylate, neopentylglycol dimethacrylate, trimethylolpropane trimethacrylate, pentaerythritol trimethacrylate, pentaerythritol tetramethacrylate, and dimethacrylate of polyoxyalkenylated bisphenol A.

The polymerizable compounds can be used singly or in combination of two or more compounds. For example, a mixture of two or more polymerizable compounds can be employed. Further, compounds formed by bonding a polymerizable group such as a vinyl group or a vinylidene group to a reducing agent or a color image forming substance are also employed as the polymerizable compounds. The light-sensitive materials employing these compounds which show functions as both of the reducing agent and the polymerizable compound, or both of the color image forming substance and the polymerizable compound are included in embodiments of the invention.

The amount of the polymerizable compound for incorporation into the light-sensitive layer preferably ranges from 5 to $1.2 \times 10^5$ times (by weight) as much as the amount of silver halide, more preferably from 10 to $1 \times 10^4$ times as much as the silver halide.

The light-sensitive material can be prepared by arranging a light-sensitive layer containing the above-mentioned components on a support. There is no limitation with respect to the support. In the case that heat development is utilized in the use of the light-sensitive material, material of the support preferably is resistant to heat given in the processing stage. Examples of the material employable for the preparation of the support include glass, paper, fine paper, coat paper, synthetic paper, metals and analogues thereof, polyester, acetyl cellulose, cellulose ester, polyvinyl acetal, polystyrene, polycarbonate, polyethylene terephthalate, and paper laminated with resin or polymer (e.g., polyethylene). In the case that a porous material, such as paper is employed as the support, the porous support preferably has such a surface characteristic that a filtered maximum waviness of not less than 4 μm is observed in not more than 20 positions among 100 positions which are determined at random on a filtered waviness curve obtained according to JIS-B-0610.

Various embodiments of the light-sensitive materials, optional components which may be contained in the light-sensitive layer, and auxiliary layers which may be optionally arranged on the light-sensitive materials are described below.

The polymerizable compound is preferably dispersed in the form of oil droplets in the light-sensitive layer. Other components in the light-sensitive layer, such as silver halide, the reducing agent, the leuco dye may be also contained in the oil droplets.

The oil droplets of the polymerizable compound are preferably prepared in the form of microcapsules. There is no specific limitation on preparation of the microcapsules.

There is also no specific limitation on shell material of the microcapsule, and various known materials such as polymers which are employed in the conventional microcapsules can be employed as the shell material. Examples of the shell material include polyamide resin and/or polyester resin, polyurea resin and/or polyurethane resin, aminoaldehide resin, gelatin, epoxy resin, a complex resin containing polyamide resin and polyurea resin, a complex resin containing polyurethane resin and polyester resin.

The mean size of the microcapsule preferably ranges from 0.5 to 50 μm, more preferably 1 to 25 μm, most preferably 3 to 20 μm. In the case that silver halide grains are contained in the microcapsule, the mean grain sized of the silver halide grains preferably is not more than the 5th part of the mean size of the microcapsules, more preferably is not more than the 10th part. It is observed that when the mean sized of the microcapsules is not less than 5 times as much as the mean grain size of silver halide grains, even and uniform image can be obtained.

In the case that silver halide grains are contained in the microcapsule, the silver halide grains are preferably arranged in the shell material of the microcapsules.

Further, two or more kinds of the microcapsules differing from each other with respect to at least one of the silver halide, the polymerizable compound and the leuco dyes can be employed. Furthermore, three or more kinds of the microcapsules differing from each other with respect to the leuco dyes including the above-mentioned leuco dye (yellow) is preferably employed to form a full color image.

The light-sensitive layer can further contain optional components such as other color image forming substances than the leuco dyes, sensitizing dyes, organic silver salts, various kinds of image formation accelerators, thermal polymerization inhibitors, thermal polymerization initiators, development stopping agents, fluorescent brightening agents, discoloration inhibitors, antihalation dyes or pigments, antiirradiation dyes or pigments, matting agents, antismudging agents, plasticizers, water releasers, binders, photo polymerization initiators and solvents of the polymerizable compound.

The light-sensitive material of the invention utilizes the leuco dye as a color image forming substance. The light-sensitive material can further contain other color image forming substance than the leuco dye. There is no specific limitation with respect to other color image forming substances, and various kinds of substances can be employed. Thus, examples of the color image forming substance include both colored substance (i.e., dyes and pigments) and non-colored or almost non-colored substance (i.e., color former or dye- or pigment-precursor) which develops to give a color under application of external energy (e.g., heating, pressing, light irradiation, etc.) or by contact with other components (i.e., developer). The light-sensitive material using the color image forming substance is described in Japanese Patent Provisional Publication No. 61(1986)-73145 (corresponding to U.S. Pat. No. 4,629,676 and European Patent Provisional Publication No. 0174634A2).

There is no specific limitation with respect to the sensitizing dyes, and known sensitizing dyes used in the conventional art of photography may be employed in the light-sensitive material. Examples of the sensitizing dyes include methine dyes, cyanine dyes, merocyanine dyes, complex cyanine dyes, complex merocyanine dyes, holopolar cyanine dyes, hemicyanine dyes, styryl dyes, and hemioxonol dyes. These sensitizing dyes can be used singly or in combination. Combinations of sensitizing dyes are often used for the purpose of supersensitization. In addition to the sensitizing dyes, a substance which does not per se exhibit spectral sensitization effect or does not substantially absorb visible light but shows supersensitizing activity can be used. The amount of the sensitizing dye to be added generally ranges from about $10^{-8}$ to about $10^{-2}$ mol per 1 mol of silver halide. The sensitizing dye is preferably added during the stage of the preparation of the silver halide emulsion (simultaneously with or after the grain formation).

When the heat development is employed in the use of the light-sensitive material, an organic silver salt is preferably contained in the light-sensitive material. It can be assumed that the organic silver salt takes part in a redox reaction using a silver halide latent image as a catalyst when heated to a temperature of 80° C. or higher. In such case, the silver halide and the organic silver salt preferably are located in contact with each other or close together. Examples of organic compounds employable for forming such organic silver salt include aliphatic or aromatic carboxylic acids, thiocarbonyl group-containing compounds having a mercapto group or an α-hydrogen atom, imino group-containing compounds, and the like. Among them, benzotriazoles are most preferable. The organic silver salt is preferably used in an amount of from 0.01 to 10 mole, and preferably from 0.01 to 1 mole, per 1 mole of the light-sensitive silver halide. Instead of the organic silver salt, an organic compound (e.g., benzotriazole) which can form an organic silver salt in combination wit an inoganic silver salt can be added to the light-sensitive layer to obtain the same effect.

Various image formation accelerators are employable in the light-sensitive material. The image formation accelerators have a function to accelerate the oxidation-reduction reaction between a silver halide (and/or an organic silver salt) and a reducing agent, a function to accelerate emigration of an image forming substance from a light-sensitive layer to an image-receiving material or an image-receiving layer, or a similar function. The image formation accelerators can be classified into inorganic bases, organic bases, base precursors, oils, surface active agents, compounds functioning as an anti-fogging agent and/or a development accelerator, hot-melt solvents, antioxidants and the like. These groups, however, generally have certain combined functions, i.e., two or more of the above-mentioned effects. Thus, the above classification is for the sake of convenience, and one compound often has a plurality of functions combined.

Various examples of these image formation accelerators are shown below.

Preferred examples of the inorganic bases include hydroxides of alkali metals or alkaline earth metals; secondary or tertiary phosphates, borates, carbonates; quinolinates and metaborates of alkali metals or alkaline earth metals; a combination of zinc hydroxide or zinc oxide and a chelating agent (e.g., sodium picolinate); ammonium hydroxide; hydroxides of quaternary alkylammoniums; and hydroxides of other metals. Preferred examples of the organic bases include aliphatic amines (e.g., trialkylamines, hydroxylamines and aliphatic polyamines); aromatic amines (e.g., N-alkyl-substituted aromatic amines, N-hydroxylalkyl-substituted aromatic amines and bis[p-(dialkylamino)phenyl]-methanes), heterocyclic amines, amidines, cyclic amidines, guanidines, and cyclic guanidines. Of these bases, those having a pKa of 7 or more are preferred.

The base precursors preferably are those capable of releasing bases upon reaction by heating, such as salts between bases and organic acids capable of decarboxylation by heating, compounds capable of releasing amines through intramolecular nucleophilic substitution, Lossen rearrangement, or Beckmann rearrangement, and the like; and those capable of releasing bases by electrolysis. Preferred examples of the base precursors include guanidine trichloroacetate, piperidine trichloroacetate, morpholine trichloroacetate, p-toluidine trichloroacetate, 2-picoline trichloroacetate, guanidine phenylsulfonylacetate, guanidine 4-chlorophenylsulfonylacetate, guanidine 4-methyl-sulfonylphenylsulfonylacetate, and 4-acetylaminomethyl propionate.

These bases or base precursors are preferably used in an amount of not more than 100% by weight, and more preferably from 0.1 to 40% by weight, based on the total solid content of the light-sensitive layer. These bases or base precursors can be used singly or in combination.

In the light-sensitive material, the silver halide, the reducing agent, the polymerizable compound and the leuco dye are preferably contained in a microcapsule and the base or base precursor is preferably arranged outside of the microcapsule in the light-sensitive layer. Further, the base or base precursor can be contained in a different microcapsule from that containing the polymerizable compound. The base or base precursor can be contained in the microcapsule under condition that the base or base precursor is dissolved or dispersed in an aqueous solution of a water retention agent, orr under condition that the base or base precursor is adsorbed on solid particles. Furthermore, the base or base precursor can be contained in a layer different from the light-sensitive layer.

Examples of the oils employable in the invention include high-boiling organic solvents which are used as solvents in emulsifying and dispersing hydrophobic compounds.

Examples of the surface active agents employable in the invention include pyridinium salts, ammonium salts and phosphonium salts as described in Japanese Patent Provisional Publication No. 59(1984)-74547; polyalkylene oxides as described in Japanese Patent Provisional Publication No. 59(1984)-57231.

The compounds functioning as an antifogging agent and/or a development accelerator are used to give a clear image having a high maximum density and a low minimum density (an image having high contrast). Examples of the compounds include a 5- or 6-membered nitrogen containing heterocyclic compound (e.g., a cyclic amide compound), a thiourea derivative, a thioether compound, a polyethylene glycol derivative, a thiol derivative, an acetylene compound and a sulfonamide derivative.

The hot-melt solvents preferably are compounds which may be used as solvent of the reducing agent or those which have high dielectric constant and can accelerate physical development of silver salts. Examples of the hot-melt solvents include polyethylene glycols, derivatives of polyethylene oxides (e.g., oleate ester), beeswax, monostearin and high dielectric constant compounds having $-SO_2-$ and/or $-CO-$ group described in U.S. Pat. No. 3,347,675; polar compounds described in U.S. Pat. No. 3,667,959; and 1,10-decanediol, methyl anisate and biphenyl suberate described in Research Disclosure 26–28 (December 1976). The light-sensitive material employing the hot-melt solvents is described in Japanese Patent Application No. 60(1985)-227527. The hot-melt solvent is preferably used in an amount of from 0.5 to 50% by weight, and more preferably from 1 to 20% by weight, based on the total solid content of the light-sensitive layer.

The antioxidants can be used to eliminate the influence of the oxygen which has an effect of inhibiting polymerization in the development process. Example of the antioxidants is a compound having two or more mercapto groups.

The thermal polymerization initiators employable in the light-sensitive material preferably are compounds that are decomposed under heating to generate a polymerization initiating species, particularly a radical, and those commonly employed as initiators of radical polymerization. The thermal polymerization initiators are described in "Addition Polymerization and Ring Opening Polymerization", pp. 6–18, edited by the Editorial Committee of High Polymer Experimental Study of the High Polymer Institute, published by Kyoritsu Shuppan (1983). Examples of the thermal polymerization initiators include azo compounds, e.g., azobisisobutyronitrile, 1,1'-azobis(1-cyclohexanecarbonitrile), dimethyl 2,2'-azobisisobutyrate, 2,2'-azobis(2-methylbutyronitrile), and azobisdimethylvaleronitrile; organic peroxides, e.g., benzoyl peroxide, di-tert-butyl peroxide, dicumyl peroxide, tert-butyl hydroperoxide, and cumene hydroperoxide; inorganic peroxides, e.g., hydrogen peroxide, potassium persulfate, and ammonium persulfate; and sodium p-toluenesulfinate. The thermal polymerization initiators are preferably used in an amount of from 0.1 to 120% by weight, and more preferably from 1 to 10% by weight, based on amount of the polymerizable compound. In a system in which the polymerizable compound within the area where the latent image has not been formed is polymerized, the thermal polymerization initiators are preferably incorporated into the light-sensitive layer. The light-sensitive material employing the thermal polymerization initiators is described in Japanese Patent Provisional Publication No. 61(1986)-260241.

The development stopping agents employable in the light-sensitive material are compounds that neutralize a base or react with a base to reduce the base concentration in the layer to thereby stop development, or compounds that mutually react with silver or a silver salt to suppress development. More specifically, examples of the development stopping agents include acid precursors capable of releasing acids upon heating electrophilic compounds capable of undergoing substitution reaction with a coexisting base upon heating, nitrogen-containing heterocyclic compounds, mercapto compounds, and the like. Examples of the acid precursors include oxide esters described in Japanese Patent Provisional Publication Nos. 60(1985)-108837 and 60(1985)-192939 and compounds which release acids through Lossen rearrangement described in Japanese Patent Provisional Publication No. 60-(1985)-230133. Examples of the electrophilic compounds which induce substitution reaction with bases upon heating are described in Japanese Patent Provisional Publication No. 60-(1985)-230134.

The antismudging agents employable in the light-sensitive material preferably are particles which are solid at ambient temperatures. Examples of the antismudging agents include starch particles described in U.K. Pat. No. 1,232,347; polymer particles described in U.S. Pat. No. 3,625,736; microcapsule particles containing no color former described in U.K. Pat. No. 1,235,991; and cellulose particles, and inorganic particles, such as particles of talc, kaolin, bentonite, agalmatolite, zinc oxide, titanium dioxide or aluminum oxide described in U.S. Pat. No. 2,711,375. Such particles preferably have a mean size of 3 to 50 μm, more preferably 5 to 40 μm. When the microcapsule is employed in the light-sensitive material, the size of said particle is preferably larger than that of the microcapsule.

Binders employable in the light-sensitive material preferably are transparent or semi-transparent hydrophilic binders. Examples of the binders include natural substances, such as gelatin, gelatin derivatives, cellulose derivatives, starch, and gum arabic; and synthetic polymeric substances, such as water-soluble polyvinyl compounds, e.g., polyvinyl alcohol, polyvinylpyrrolidone, and acrylamide polymers. In addition to the synthetic polymeric substances, vinyl compounds dispersed in the form of latex, which are particularly effective to increase dimensional stability of photographic materials, can be also used. These binders can be used singly or in combination. The light-sensitive material employing a binder is described in Japanese Patent Provisional Publication No. 61(1986)-69062 (corresponding to U.S. Pat. No. 4,629,676 and European Patent Provisional Publication No. 0174634A2).

A photo polymerization initiator can be contained in the light-sensitive layer to polymerize the unpolymerized polymerizable compound after the image-formation.

In the case that the solvent of the polymerizable compound is used, the solvent is preferably contained in a microcapsule which is different from the microcapsule containing the polymerizable compound.

Examples and usage of the other optional components which can be contained in the light-sensitive layer are also described in the above-mentioned publications and applications concerning the light-sensitive material, and in Research Disclosure Vol. 170, No. 17029, pp. 9–15 (June 1978).

Examples of auxiliary layers which are optionally arranged on the light-sensitive material include an image-receiving layer, a heating layer, an antistatic layer, an anticurl layer, a release layer, a cover sheet or a protective layer, a layer containing a base or base precursor and a base barrier layer.

Instead of the use of the image-receiving material, the image-receiving layer can be arranged on the light-sensitive material to produce the desired image on the image-receiving layer of the light-sensitive material. The image-receiving layer of the light-sensitive material can be constructed in the same manner as the layer of the image-receiving layer.

The light-sensitive material can be prepared, for instance, by the following process.

The light-sensitive material is usually prepared by dissolving, emulsifying or dispersing each of the components of the light-sensitive layer in an adequate medium to obtain coating solution, and then coating the obtained coating solution on a support.

The coating solution can be prepared by mixing liquid compositions each containing a component of the light-sensitive layer. Liquid composition containing two or more components may be also used in the preparation of the coating solution. Some components of the light-sensitive layer can be directly added to the coating solution or the liquid composition. Further, a secondary composition can be prepared by emulsifying the oily (or aqueous) composition in an aqueous (or oily) medium to obtain the coating solution.

The silver halide is preferably prepared in the form of a silver halide emulsion. Various processes for the preparation of the silver halide emulsion are known in the conventional technology for the preparation of photographic materials.

The silver halide emulsion can be prepared by the acid process, neutral process or ammonia process. In the stage for the preparation, a soluble silver salt and a halogen salt can be reacted in accordance with the single jet process, double jet process or a combination thereof. A reverse mixing method, in which grains are formed in the presence of excess silver ions, or a controlled double jet process, in which a pAg value is maintained constant, can be also employed. In order to accelerate grain growth, the concentrations or amounts or the silver salt and halogen salt to be added or the rate of their addition can be increased as described in Japanese Patent Provisional Publication Nos. 55(1980)-142329 and 55(1980)-158124, and U.S. Pat. No. 3,650,757, etc.

The silver halide emulsion may be of a surface latent image type that forms a latent image predominantly on the surface of silver halide grains, or of an inner latent image type that forms a latent image predominantly in the interior of the grains. A direct reversal emulsion comprising an inner latent image type emulsion and a nucleating agent may be employed. The inner latent image type emulsion suitable for this purpose is described in U.S. Pat. Nos. 2,592,250 and 3,761,276, Japanese Patent Publication No. 58(1983)-3534 and Japanese Patent Provisional Publication No. 57(1982)-136641, etc. The nucleating agent that is preferably used in combination with the inner latent image type emulsion is described in U.S. Pat. Nos. 3,227,552, 4,245,037, 4,255,511, 4,266,013 and 4,276,364, and West German Patent Provisional Publication (OLS) No. 2,635,316.

In the preparation of the silver halide emulsions, hydrophilic colloids are advantageously used as protective colloids. Examples of usable hydrophilic colloids include proteins, e.g., gelatin, gelatin derivatives, gelatin grafted with other polymers, albumin, and casein; cellulose derivatives, e.g., hydroxyethyl cellulose, carboxymethyl cellulose, cellulose sulfate, etc.; saccharide derivatives, e.g., sodium alginate and starch derivatives; and a wide variety of synthetic hydrophilic polymers, such as polyvinyl alcohol, polyvinyl alcohol partial acetal, poly-N-vinylpyrrolidone, polyacrylic acid, polymethacrylic acid, polyacrylamide, polyvinylimidazole, and polyvinylpyrazole, and copolymers comprising monomers constituting these homopolymers. Among them, gelatin is most preferred. Examples of employable gelatins include not only lime-processed gelatin, but also acid-processed gelatin and enzyme-processed gelatin. Hydrolysis products or enzymatic decomposition products of gelatin can also be used.

In the formation of silver halide grains in the silver halide emulsion, ammonia, an organic thioether derivative as described in Japanese Patent Publication No. 47(1972)-11386 or sulfur-containing compound as described in Japanese Patent Provisional Publication No. 53(1978)-144319 can be used as a silver halide solvent. Further, in the grain formation or physical ripening, a cadmium salt, a zinc salt, a lead salt, a thallium salt, or the like can be introduced into the reaction system. Furthermore, for the purpose of improving high or low intensity reciprocity law failure, a water-soluble iridium salt, e.g., iridium (III) or (IV) chloride, or ammonium hexachloroiridate, or a water-soluble rhodium salt, e.g., rhodium chloride can be used.

After the grain formation or physical ripening, soluble salts may be removed from the resulting emulsion by a known noodle washing method or a sedimentation method. The silver halide emulsion may be used in the primitive condition, but is usually subjected to chemical sensitization. Chemical sensitization can be carried out by the sulfur sensitization, reduction sensitization or noble metal sensitization, or a combination thereof that are known for emulsions for the preparation of the conventional light-sensitive materials.

When the sensitizing dyes are added to the silver halide emulsion, the sensitizing dye is preferably added during the preparation of the emulsion. When the organic silver salts are introduced in the light-sensitive microcapsule, the emulsion of the organic silver salts can be prepared in the same manner as in the preparation of the silver halide emulsion.

In preparation of the light-sensitive material, the polymerizable compounds are used as the medium for preparation of the liquid composition containing another component of the light-sensitive layer. For example, the silver halide, including the silver halide emulsion), the reducing agent, or the leuco dye can be dissolved, emulsified or dispersed in the polymerizable compound to prepare the light-sensitive material. Especially, the leuco dye is preferably incorporated in the polymerizable compound. Further, the necessary components for preparation of a microcapsule, such as shell material can be incorporated into the polymerizable compound.

The light-sensitive composition which is the polymerizable compound containing the silver halide can be prepared using the silver halide emulsion. The light-sensitive composition can be also prepared using silver halide powders which can be prepared by lyophilization. These light-sensitive composition can be obtained by stirring the polymerizable compound and the silver halide using a homogenizer, a blender, a mixer or other conventional stirring device.

Polymers having a principal chain consisting essentially of a hydrocarbon chain substituted in part with hydrophilic groups which contain, in their terminal groups, —OH or nitrogen having a lone electron-pair are preferably introduced into the polymerizable compound prior to the preparation of the light-sensitive composition. The polymer has a function of dispersing silver halide or other component in the polymerizable compound very uniformly as well as a function of keeping thus dispered state. Further, the polymer has another function of gathering silver halide along the interface between the polymerizable compound (i.e., light-sensitive composition) and the aqueous medium in preparation of the microcapsule. Therefore, using this polymer, silver halide can be easily introduced into the shell material of the microcapsule.

The light-sensitive composition can be also prepared by dispersing microcapsules containing silver halide emulsion as a core structure in the polymerizable compound instead of employing the above polymer.

The polymerizable compound (including the light-sensitive composition) are preferably emulsified in an aqueous medium to prepare the coating solution. The necessary components for preparation of the microcapsule, such as shell material can be incorporated into the emulsion. Further, other components such as the reducing agent can be added to the emulsion.

The emulsion of the polymerizable compound can be processed for forming shell of the microcapsule. Examples of the process for the preparation of the microcapsules include a process utilizing coacervation of hydrophilic wall-forming materials as described in U.S. Pat. Nos. 2,800,457 and 2,800,458; an interfacial polymerization process as described in U.S. Pat. No. 3,287,154, U.K. Pat. No. 990,443 and Japanese Patent Publication Nos. 38(1963)-19574, 42(1967)-446 and 42(1967)-771; a process utilizing precipitation of polymers as described in U.S. Pat. Nos. 3,418,250 and 3,660,304; a process of using isocyanate-polyol wall materials as described in U.S. Pat. No. 3,796,669; a process of using isocyanate wall materials as described in U.S. Pat. No. 3,914,511; a process of using urea-formaldehyde or urea-formaldehyde-resorcinol wall-forming materials as described in U.S. Pat. Nos. 4,001,140, 4,087,376 and 4,089,802; a process of using melamine-formaldehyde resins hydroxypropyl cellulose or like wall-forming materials as described in U.S. Pat. No. 4,025,455; an in situ process utilizing polymerization of monomers as described in U.K. Pat. No. 867,797 and U.S. Pat. No. 4,001,140; an electrolytic dispersion and cooling process as described in U.K. Pat. Nos. 952,807 and 965,074; a spray-drying process as described in U.S. Pat. No. 3,111,407 and U.K. Pat. No. 930,422; and the like. It is preferable, though not limitative, that the microcapsule is prepared by emulsifying core materials containing the polymerizable compound and forming a polymeric membrane (i.e., shell) over the core materials.

When the emulsion of the polymerizable compound (including the dispersion of the microcapsule) has been prepared by using the light-sensitive composition, the emulsion can be used as the coating solution of the light-sensitive material. The coating solution can be also prepared by mixing the emulsion of the polymerizable compound and the silver halide emulsion. The other components can be added to the coating solution in a similar manner as the emulsion of the polymerizable compound.

A light-sensitive material of the invention can be prepared by coating and drying the above-prepared coating solution on a support in the conventional manner.

The image-forming method employing the light-sensitive material of the invention is described below.

In the use of the light-sensitive material of the invention, a development process is conducted simultaneously with or after an imagewise exposure.

Various exposure means can be employed in the imagewise exposure, and in general, the latent image on the silver halide is obtained by imagewise exposure to radiation including visible light. The type of light source and exposure can be selected depending on the light-sensitive wavelengths determined by spectral sensitization or sensitivity of silver halide. Original image can be either monochromatic image or color image.

Development of the light-sensitive material can be conducted simultaneously with or after the imagewise exposure. The development can be conducted using a developing solution in the same manner as the image forming method described in Japanese Patent Publication No. 45(1970)-11149. The image forming method described in Japanese Patent Provisional Publication No. 61(1986)-69062 which employs a heat development process has an advantage of simple procedures and short processing time because of the dry process. Thus, the latter method is preferred as the development process of the light-sensitive material.

Heating in the heat development process can be conducted in various known manners. The heating layer which is arranged on the light-sensitive material can be used as the heating means in the same manner as the light-sensitive material described in Japanese Patent Provisional Publication No. 61(1986)-294434. Further, the light-sensitive material can be heated while suppressing supply of oxygen into the light-sensitive layer from outside. Heating temperatures for the development process usually ranges from 80° C. to 200° C., and preferably from 100° C. to 160° C. Various heating patterns are applicable. The heating time is usually not shorter than 1 second, preferably from 1 second to 5 minutes, and more preferably from 1 second to 1 minute.

During the above development process, a polymerizable compound within the area where a latent image of the silver halide has been formed or within the area where a latent image of the silver halide has not been formed is polymerized. In a general system, the polymerizable compound within the area where the latent image has been formed is polymerized. If a nature or amount of the reducing agent is controlled, the polymerizable compound within the area where the latent image has not been formed can be polymerized.

In the above development process, the leuco dye can be fixed on the support by the polymerization.

Where the leuco dye and the polymerizable compound are contained in a microcapsule, and the acid color developer is arranged outside of the microcapsule in the light-sensitive layer, a color image (yellow) can be formed on the light-sensitive material of the invention by pressing the material after the development process.

The image is preferably formed on the image-receiving material. The image-receiving material is described hereinbelow. The image forming method employing the image-receiving material or the image-receiving layer is described in Japanese Patent Provisional Publication No. 61(1986)-278849.

Examples of the materials employable as the support of the image-receiving material include baryta paper in addition to various examples which can be employed as the support of the above mentioned light-sensitive material. In the case that a porous material, such as paper is employed as the support of the image-receiving material, the porous support preferably has such a surface characteristic that a filtered maximum waviness of not less than 4 μm is observed in not more than 20 positions among 100 positions which are determined at random on a filtered waviness curve obtained according to JIS-B-0610. Further, a transparent material can be employed as the support of the image-receiving material to obtain a transparent or a projected image.

The image-receiving material is usually prepared by providing the image-receiving layer on the support. In the case that the light-sensitive layer contains the acid color developer to develop the leuco dyes previous to or simultaneously with the transference of the leuco dyes to the image-receiving material, the image-receiving material be composed of a simple support.

The image-receiving layer can contain the acid color developer according to the color formation system of the above mentioned leuco dyes. As mentioned above, the acid color developer is preferably contained in the image-receiving layer.

The image-receiving layer preferably contains a polymer as binder. The binder which may be employed in the above-mentioned light-receiving layer is also employable in the image-receiving layer. Further, a polymer having a transmission coefficient of oxygen of not more than $1.0 \times 10^{-11}$ cm$^3$.cm/cm$^2$.sec.cmHg can be used as the binder to protect the color of the image formed on the image-receiving material.

The image-receiving layer can contain a granulated thermoplastic compound to obtain a glossy image. Further, the image-receiving layer can contain a white pigment (e.g., titanium dioxide) to function as a white reflection layer. Furthermore, a photo polymerization initiator or a thermalpolymerization initiator can be contained in the image-receiving layer to polymerize the unpolymerized polymerizable compound.

The image-receiving layer can be composed of two or more layers according to the above-mentioned functions. The thickness of the image-receiving layer preferably ranges from 1 to 100 μm, more preferably from 1 to 20 μm.

A protective layer can be provided on the surface of the image-receiving layer.

After the development process, pressing the light-sensitive material of the invention on the the image-receiving material to transfer the unfixed leuco dyes to the image-receiving material, a color image can be produced in the image-receiving material. The process for pressing can be carried out in various known manners.

As mentioned above, the reaction of the leuco dye with the acid color developer can be accelerated by heating. Therefore, the image-receiving material is preferably heated after the transference of the leuco dye to the image-receiving material.

This process for heating the image-receiving material after the transference has another advantage of polymerizing the unpolymerized polymerizable compound which has been transferred with the leuco dye to improve preservability of the obtained image.

The light-sensitive material can be used for monochromatic or color photography, printing, radiography, diagnosis (e.g., CRT photography of diagnostic device using supersonic wave), copy (e.g., computer-graphic hard copy), etc.

While the typical recording material (light-sensitive material) of the invention has been described above, the recording material of the invention can be used as other recording materials such as a pressure-sensitive material, a heat-sensitive material, an electrothermal recording sheet, an ultrasonic recording sheet, an electron beam recording material and an electrostatic recording material.

The pressure-sensitive material of the invention is described in more detail hereinbelow.

The pressure-sensitive material generally comprises a layer (or sheet) containing the leuco dye and a layer (or sheet) containing the acid color developer. The sheet comprises a layer containing the leuco dye or the acid color developer provided on a support.

The layer containing the leuco dye preferably contains a binder. The leuco dye is preferably contained in microcapsules which are dispersed in the layer.

The microcapsules containing the leuco dye can be prepared in the following manner.

The leuco dye is dissolved or dispersed in an appropriate organic solvent and the resulting solution or dispersion (oil liquid) is emulsified in an aqueous medium.

The organic solvent preferably has a boiling point of not lower than 180° C., because a low-boiling organic silvent suffers an evaporation loss during storage. Examples of the organic solvents include an phosphoric ester, a phthalic ester, a carboxylic acid ester, a fatty acid amide, an alkylated biphenyl, an alkylated terphenyl, a chlorinated paraffin and a diarylethanol.

Concrete examples of the organic solvents include tricresyl phosphate, trioctyl phosphate, octyl diphenyl phosphate, tricyclohexyl phosphate, dibutyl phthalate, dioctyl phthalate, dilauryl phthalate, dicyclohexyl phthalate, butyl oleate, diethylene glycol dibenzoate, dioctyl sebacate, dibutyl sebacate, dioctyl adipate, trioctyl trimellitate, acetyltriethyl citrate, octyl maleate, dibutyl maleate, isopropylbiphenyl, isoamylbiphenyl, chlorinated paraffin, diisopropylnaphthalene, 1,1'-ditolylethane, 2,4-di-tert-amylphenol and N,N-dibutyl-2-butoxy-5-tert-octylaniline. A vinyl compound can be also used as the organic solvent.

The leuco dye of the invention is preferably used in an amount of from 2 to 20 weight % based on the amount of the organic solvent.

The oil droplets in the emulsion is then processed for forming shell of the microcapsules.

There is no specific limitation on shell material of the microcapsule, and various known materials such as polymers can be employed as the shell material. Examples of the shell material include polyurethane, polyurea, polyamide, polyester, urea/formaldehyde resin, melamin resin, polystyrene, styrene/methacrylate copolymer, styrene/acrylate copolymer and mixtures thereof.

The microcapsule can be prepared by any of conventional methods without specific limitations. However an interfacial polymerization method and an internal polymerization method are preferred in the invention.

Where polyurea and/or polyurethane is used as the shell material of the microcapsule, a polyisocyanate is mixed with a second material capable of reacting with the polyisocyanate to form the shell (e.g., polyol or polyamine) in an aqueous medium or an oil liquid to be encapsulated and the mixture is emulsified and dispersed in water and then heated. Thus, a polymerization reaction takes place at the interface of oil droplets to form the shell of the microcapsule.

In the process for formation of the microcapsule, a water-soluble polymer can be used as a protective colloid. The water-soluble polymer is preferably anionic, nonionic or amphoteric.

The anionic polymer used as the protective colloid may be either a natural substance or a synthetic substance. The anionic polymer preferably has carboxyl group or sulfo group. Examples of the anionic polymers include natural substances such as gum arabic and alginic acid; semisynthetic substances such as carboxymethylcellulose, phthalated gelatin, sulfated starch, cellulose sulfate and lignin sulfonic acid; and synthetic substances such as a maleic anhydride copolymer and hydrolysis products thereof, a (meth)acrylic acid polymer and copolymers thereof, a vinylbenzene-sulfonic acid polymer and copolymers thereof and a carboxy-modified polyvinyl alcohol. Examples of the nonionic polymers include polyvinyl alcohol, hydroxyethylcellulose and methylcellulose. An example of the amphoteric polymer is gelatin.

These water-soluble polymers (protective colloids) are preferably used in the form of an aqueous solution. The polymer is preferably contained in the solution in an amount of 0.01 to 10 weight %.

Examples of the binder which can be used in the layer containing the leuco dye include polyvinyl alcohol, methylcellulose, carboxymethylcellulose, hydroxypropylcellulose, gum arabic, gelatin, polyvinyl pyrrolidone, casein, styrene/butadiene latex, acrylonitrile/butadiene latex, polyvinyl acetate, polyacrylic ester and ethylene/vinyl acetate copolymer. These binders are preferably used in the form of an emulsion.

The binder is used in an amount of 0.5 to 5 g/m$^2$ on a solid basis.

The layer containing the leuco dye can be formed in such a manner that a microcapsule dispersion is mixed with a binder solution to prepare a coating solution and the coating solution is coated on a support according to a conventional coating method, such as bar coating, blade coating, air-knife coating, gravure coating, roll coating, spray coating and dip coating methods, and then dried.

The layer containing the leuco dye is usually provided in a range of 2.5 to 25 g/m$^2$ on a solid basis.

A paper support is preferably employed in the pressure sensitive material. A neutral paper having a pH of 6 to 9, which is measured according to a hot water extracting method, is preferably used as the paper support from the viewpoint of the storage stability of the recording material. The neutral paper support can be prepered, for instance, using a neutral size such as an alkylketene dimer. The surface of the paper support may be treated. The neutral paper support is described in more detail in Japanese Patent Provisional Publication No. 55(1980)-14281.

The layer (or sheet) containing the acid color developer can be formed in such a manner that an emulsion of the acid color developer is mixed with a binder to prepare a coating solution and the coating solution is coated on a support in a similar manner to that described above and then dried. The binder may be the same as that of the layer containing the leuco dye. The sheet containing the developer can be prepared using a different support from that of the pressure sensitive material.

The pressure-sensitive material containing a leuco dye is usually laminated on the sheet containing an acid color developer prior to use.

There are various embodiments other than that mentioned above. For instance, the leuco dye can be contained in different microcapsules from those containing the acid color developer and the two kinds of the microcapsules can be contained in the same layer (or sheet layer). In other embodiment, the leuco dye can be contained in a different layer from that containing the acid color coupler and both layers are provided on the same support. In this embodiment, the pressure-sensitive material has a multilayer structure.

In the recording process employing the pressure-sensitive material of the present invention, external pressure, for instance handwriting or typewriting pressure breaks the microcapsules and releases the leuco dye, which reacts with the acid color developer to produce visible color.

The heat-sensitive material (thermal recording material) of the invention is described in more detail hereinbelow.

The heat-sensitive material has basically the same structure as that of the aforementioned pressure-sensitive material. The heat-sensitive recording material comprises a heat-sensitive layer (thermal recording layer) provided on a support. The leuco dye of the invention contained in the heat-sensitive layer. The acid color developer is preferably contained in the same layer as that of the leuco dye in consideration of saving thermal energy required for thermal response and color formation. The leuco dye is preferably contained in microcapsules which are dispersed in the heat-sensitive layer.

The shell material of the microcapsule preferably is a polymer which is impermeable at room temperature and becomes permeable at an elevated temperature. The polymer more preferably has a glass transition temperature of from 60° to 200° C. The shell material most preferably is polyurea or polyurethane.

The thermal recording process employing the heat-sensitive material of the invention is carried out, for instance, in the following manner.

The heat-sensitive material is arranged such that it is in contact with a heating element (printing head) such as thermal needle or thermal head. The heating element is heated in series corresponding to electric signals having image information transmitted from facsimile or electronic computer, and it scans the heat-sensitive material in a direction at the same time while it is in contact with the material. When the heat-sensitive material is moved in a direction perpendicular to the scanning direction of the heating element, a two-dimensional printing or image can be formed on the heat-sensitive material.

The present invention is further described by the following examples without limiting the invention thereto. In the following examples, "part(s)" means "part(s) by weight", unless otherwise indicated.

EXAMPLE 1

Preparation of silver halide emulsion

In 1,000 ml of water were dissolved 20 g of gelatin and 3 g of sodium chloride, and the resulting gelatin solution was kept at 75° C. To the gelatin solution, 600 ml of an aqueous solution containing 21 g of sodium chloride and 56 g of potassium bromide and 600 ml of an aqueous solution containing 0.59 mole of silver nitrate were added simultaneously at the same feed rate over a period of 40 minutes to obtain a silver chlorobromide emulsion having cubic grains, uniform grain size distribution, mean grain size of 0.35 μm and bromide content of 80 mole %.

The emulsion was washed for desalting and then subjected to chemical sensitization with 5 mg of sodium thiosulfate and 20 mg of 4-hydroxy-6-methyl-1,3,3a,7-tetraazaindene at 60° C. The yield of the emulsion was 600 g.

Preparation of silver benzotriazole emulsion

In 3,000 ml of water were dissolved 28 g of gelatin and 13.2 g of benzotriazole, and the solution was kept at 40° C. while stirring. To the solution was added 100 ml of an aqueous solution of 17 g of silver nitrate over 2 minutes. Excessive salts were sedimented and removed from the resulting emulsion by pH-adjustment. Thereafter, the emulsion was adjusted to pH 6.30 to obtain a silver benzotriazole emulsion. The yield of the emulsion was 400 g.

Preparation of light-sensitive composition

In 100 g of trimethylolpropane triacrylate were dissolved 0.40 g of the following copolymer, 6 g of the following leuco dye (1) and 2 g of Emulex NP-8 (tradename of Nippon Emulsion Co., Ltd.).

(Copolymer)

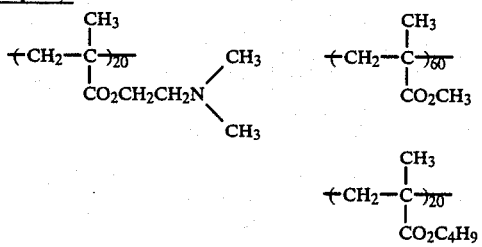

(Leuco dye (1))

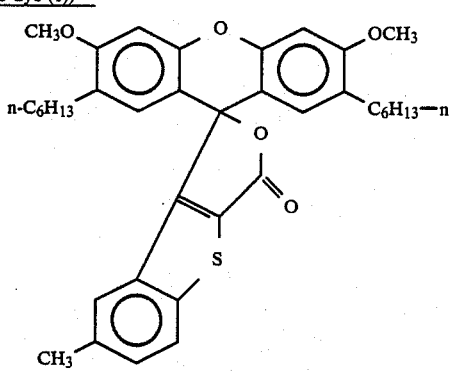

to 18.00 g of the resulting solution was added a solution in which 0.16 g of the following reducing agent (I) and 1.22 g of the following reducing agent (II) are dissolved in 1.80 g of methylene chloride.

(Reducing agent (I))

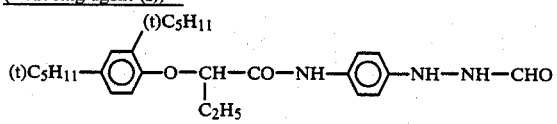

(Reducing agent (II))

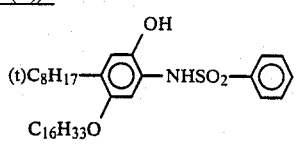

To the mixture were further added 3.50 g of the silver halide emulsion and 3.35 g of the silver benzotriazole emulsion, and the mixture was stirred at 15,000 r.p.m. for 5 minutes using a homogenizer to obtain a light-sensitive composition.

Preparation of light-sensitive microcapsule

To 10.51 g of 18.6% aqueous solution of Isobam (tradename of Kuraray Co., Ltd.) was added 48.56 g of 2.89% aqueous solution of pectin. After the solution was adjusted to a pH of 4.0 using 10% sulfuric acid, the light-sensitive composition was added to the resulting solution, and the mixture was stirred at 7,000 r.p.m. for 2 minutes to emulsify the light-sensitive composition in the aqueous medium.

To 72.5 g of the aqueous emulsion were added 8.32 g of 40% aqueous solution of urea, 2.82 g of 11.3% aqueous solution of resorcinol, 8.56 g of 37% aqueous solution of formaldehyde, and 2.74 g of 8.76% aqueous solution of ammonium sulfate in this order, and the mixture was heated at 60° C. for 2 hours while stirring. After the mixture was adjusted to a pH of 7.0 using 10% aqueous solution of sodium hydroxide, 3.62 g of 30.9% aqueous solution of sodium hydrogen sulfite was added to the mixture to obtain a dispersion containing light-sensitive microcapsules.

Preparation of light-sensitive material

To 10.0 g of the light-sensitive microcapsule dispersion were added 1.0 g of 1% aqueous solution of the following anionic surfactant and 1.0 g of 10% solution (solvent: water/ethanol=50/50 as volume ratio) of guanidine trichroloacetate to prepare a coating solution.

(Anionic surfactant)

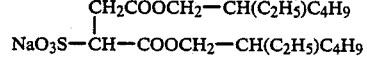

The coating solution was uniformly coated on a polyethylene terephthalate film (thickness: 100 μm) using a coating rod of #40 to give a layer having a wet thickness of 70 μm and dried at about 40° C. to obtain a light-sensitive material (A).

EXAMPLE 2

Light-sensitive materials (B) to (D) were prepared in the same manner as in Example 1 except that the following leuco dyes (4), (6) and (14) were respectively used in place of the leuco dye (1).

(Leuco Dye (4))

-continued (Leuco Dye (6))

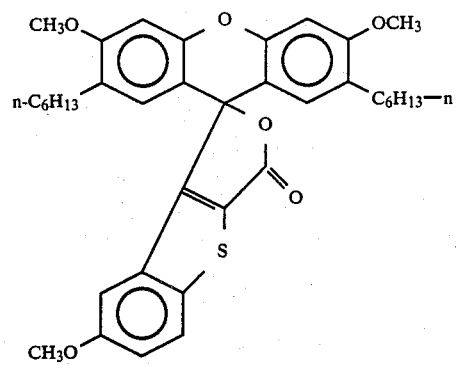

(Leuco Dye (14))

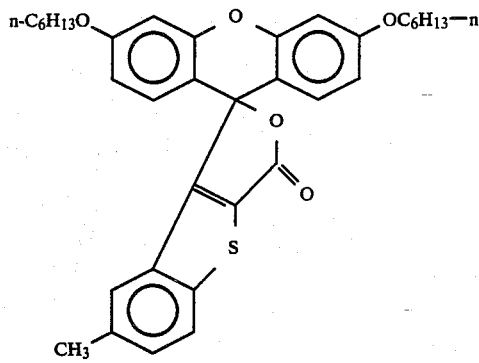

COMPARISON EXAMPLE 1

Light-sensitive materials (E) and (F) were prepared in the same manner as in Example 1 except that the following conventional leuco dyes (a) and (b) were respectively used in place of the leuco dye (1).

(Leuco Dye (a))

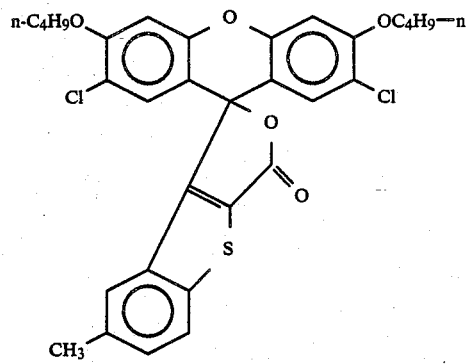

-continued (Leuco Dye (b))

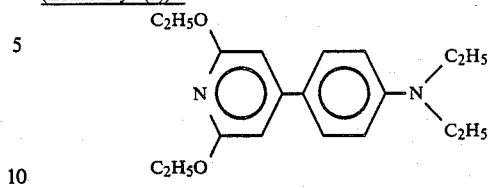

Preparation of image-receiving material

To 125 g of water was added 11 g of 40% aqueous solution of sodium hexametaphosphate, and to the mixture were further added 34 g of zinc 3,5-di-α-methyl-benzylsalicylate and 82 g of 55% slurry of calcium carbonate, followed by coarsely dispersing in a mixer.

The coarse dispersion was then finely dispersed in Dynomill dispersing device. To 200 g of the resulting dispersion were added 6 g of 50% latex of SBR (styrene-butadiene rubber) and 55 g of 8% aqueous solution of polyvinyl alcohol, and the resulting mixture was made uniform. The mixture was then uniformly coated on an art paper having basis weight of 43 g/m² to give a layer having wet thickness of 30 μm and dried to obtain an image-receiving material.

Evaluation of light-sensitive material

Each of the light-sensitive materials (A) to (F) prepared in Examples 1 & 2 and Comparison Example 1 was imagewise exposed to light using a tungsten lamp at 200 lux for 1 second and then heated on a hot plate at 125° C. for 30 seconds. Each of the exposed and heated light-sensitive materials was then combined with the image-receiving material and passed through press rolls at pressure of 350 kg/cm². The density of the positive color image (yellow color image) obtained on the image-receiving material was measured using a reflection densitometer.

Further, the light fastness of the obtained image was evaluated according to the following manner.

Each of the image-receiving materials on which the image had been formed was irradiated with light using a zenon lamp at 80,000 lux for 8 hours. And then, the discoloration was evaluated measuring the density of the remaining color image and cmparing the density with that before the irradiation.

The results are set forth in Table 1. In Table 1, "Remaining Ratio after Irradiation" means the ratio of the density of the color image after the irradiation to that before the irradiation.

TABLE 1

| Light-Sensitive Material | Leuco Dye | Maximum Density | Minimum Density | Remaining Ratio after Irradiation |
|---|---|---|---|---|
| (A) | (1) | 1.30 | 0.08 | 98% |
| (B) | (4) | 1.31 | 0.13 | 98% |
| (C) | (6) | 1.27 | 0.10 | 95% |
| (D) | (14) | 1.29 | 0.09 | 90% |
| (E) | (a) | 1.05 | 0.12 | 80% |
| (F) | (b) | 0.82 | 0.15 | 63% |

It is apparent from the results in Table 1 that each of the light-sensitive materials (A) to (D) according to the invention gives an improved positive image which has a high maximum density and a low minimum density compared with the light-sensitive materials (E) and (F)

containing conventional leuco dyes. Further, it is also apparent that each of the light-sensitive materials of the invention gives an image improved in the light fastness.

EXAMPLE 3

Preparation of heat-sensitive material

In 95 parts of hot water at about 80° C. was dissolved 5 parts of partial sodium salt of polyvinylbenzenesulfonic acid (VERSA, TL500, average molecular weight; 500,000; produced by National Starch Co.) while stirring over 30 minutes. The aqueous solution was then cooled. The resulting aqueous solution having a pH of from 2 to 3 was adjusted to pH of 4.0 using 20 weight % aqueous solution of sodium hydroxide.

In 100 parts of the obtained 5% aqueous solution of partial sodium salt of polyvinylbenzenesulfonic acid was emulsified 100 parts of 3.5 weight % diisopropylnaphthalene solution of the following leuco dye (1) to obtain an emulsion having average droplet size of 4.5 μm.

(Leuco Dye (1))

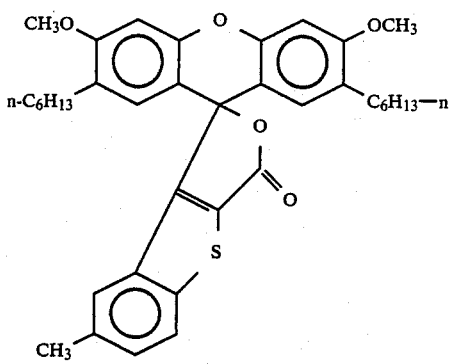

Separately, 6 parts of melamine, 11 parts of 37 weight % aqueous solution of formaldehyde and 30 parts of water were heated to 60° C. while stirring. After 30 minutes, a clear aqueous solution of a mixture (precondensate) of melamine, formaldehyde and a malamineformaldehyde precondensate was obtained. The aqueous solution had a pH of 6 to 8.

To the emulsion was added the precondensate solution obtained above. The resulting mixture was adjusted to pH of 6.0 using 3.6 weight % aqueous solution of phosphoric acid while stirring. The mixture was then heated to 65° C. while stirring for 6 hours to obtain a microcapsule dispersion. The dispersion was then cooled to room temperature and adjusted to pH of 9.0 using 20 weight % aqueous solution of sodium hydroxide.

To the microcapsule dispersion were added 200 parts of 10 weight % aqueous solution of polyvinyl alcohol (PVA-117, produced by Kuraray Co., Ltd.) and 50 parts of starch particles. To the mixture was further added water to obtain a coating solution having solid content of 20 %. The coating solution was coated on the surface of a base paper having basis weight of 50 g/m² in coating amount of 5 g/m² based on the solid content using an air-knife coater and then dried to obtain a pressure-sensitive material (G).

EXAMPLE 4

A pressure-sensitive material (H) was prepared in the same manner as in Example 3, except that the following leuco dye (4) was used in place of the leuco dye (1).

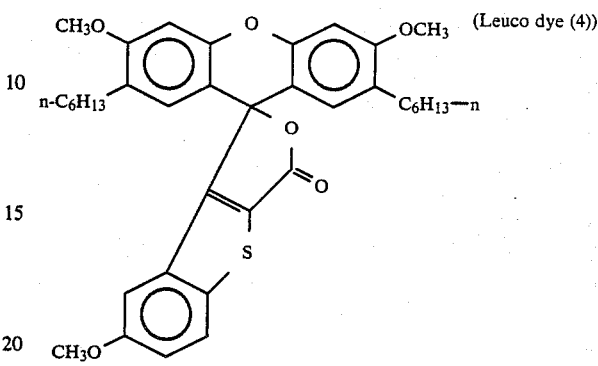
(Leuco dye (4))

Preparation of sheet containing acid color developer

To 20 parts of 1-isopropylphenyl-2-phenylethane was added 10 parts of zinc 3,5-bis-α-methylbenzylsalicylate, and the mixture was heated at 90° C. to obtain a solution. The solution was added to 50 parts of 2 weight % aqueous solution of polyvinyl alcohol (PVA-117; produced by Kuraray Co., Ltd.) and 0.1 part of 10% aqueous solution of triethanolamine dodecylbenzenesulfonate (surfactant) was further added to the mixture. The resulting mixture was stirred using a homogenizer to obtain an emulsion having average droplet size of 3 μm.

A dispersion containing 80 parts of calsium carbonate and 20 parts of zinc oxide was prepared using kedy mill, and to the emulsion was mixed the dispersion. To the mixture were further added 100 parts of 10 weight % aqueous solution of polyvinyl alcohol (PVA-117; produced by Kuraray Co., Ltd.) as binder and 10 parts of a carboxy-modified SBR latex (SN-307; produced by Sumitomo Naugatax Co.) as solid content. To the mixture was then added water to obtain a coating solution (I) having solid content of 20%.

Separately, a mixture containing 10 parts of zinc 3,5-bis-α-methyl-benzylsalicylate, 20 parts of silton clay, 60 parts of calcium carbonate, 20 parts of zinc oxide, 1 part of sodium hexametaphosphate and 200 parts of water was stirred using a sand grinder to obtain a dispersion having average particle size of 3 μm.

To the resulting dispersion was added 16 parts of a 10 weight % aqueous solution of polyvinyl alcohol (PVA-103; produced by Kuraray Co., Ltd.). To the mixture were added 100 parts of 10 weight % aqueous solution of polyvinyl alcohol (PVA-117; produced by Kuraray Co., Ltd.) and 10 parts of carboxy-modified SBR latex (SN-307; produced by Sumitomo Naugatax Co.) as solid content. To the mixture was then added water to obtain a coating solution (II) having solid content of 20%.

The coating solution (I) was mixed with the coating solution (II) in the ratio of 50 (I) to 50 (II) in terms of the amount of acid color developer. The mixture was coated on the surface of a base paper base having basis weight of 50 g/m² in coating amount of 5.0 g/m² based on the solid content using an air-knife coater and then dried to obtain a sheet containing an acid color developer.

Evaluation of pressure-sensitive material

Each of the pressure-sensitive materials (G) and (H) was pressed on the sheet containing an acid color developer and the density of each of the yellow images obtained on the sheet was measured using a reflection densitometer.

The results are set forth in Table 2.

TABLE 2

| | Pressure-sensitive Material | Leuco Dye | Density of Developed Color |
|---|---|---|---|
| Example 3 | (G) | (1) | 0.89 |
| Example 4 | (H) | (4) | 0.91 |

It is apparent from the results in Table 2 that each of the pressure-sensitive materials of the present invention (G) and (H) gives an improved color image in which the density of the developed color is high. Further, it is observed that the color developing rate is also improved in the pressure-sensitive materials (G) and (H).

We claim:

1. A recording material comprising a layer containing a leuco dye provided on a support, wherein the leuco dye has the formula (I):

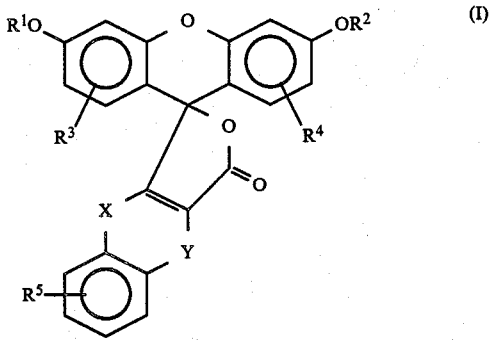

in which one of X and Y is a single bond and the other is sulfur atom; each of $R^1$ and $R^2$ independently is a monovalent group selected from the group consisting of an alkyl group, a cycloalkyl group and an aralkyl group; each of $R^3$ and $R^4$ independently is a monovalent group selected from the group consisting of hydrogen, a halogen atom, an alkyl group, an alkoxy group, a cycloalkyl group, an aralkyl group and an aryloxy group; $R^5$ is a monovalent group selected from the group consisting of hydrogen, a halogen atom, an alkyl group, an alkoxy group, nitro and amino; and each of $R^1$, $R^2$, $R^3$, $R^4$ and $R^5$ may have one or more substituent groups.

2. The recording material as claimed in claim 1, wherein the recording material comprises a light-sensitive layer containing silver halide, a reducing agent, a polymerizable compound and the leuco dye provided on a support.

3. The recording material as claimed in claim 2, wherein the polymerizable compound and the leuco dye are contained in microcapsules which are dispersed in the light-sensitive layer.

4. The recording material as claimed in claim 2, wherein the silver halide, the polymerizable compound and the leuco dye are contained in microcapsules which are dispersed in the light-sensitive layer.

5. The recording material as claimed in claim 2, wherein the silver halide, the reducing agent, the polymerizable compound and the leuco dye are contained in microcapsules which are dispersed in the light-sensitive layer.

6. The recording material as claimed in claim 2, wherein the leuco dye is contained in an amount of from 0.5 to 50 weight % based on the amount of the polymerizable compound in the light-sensitive layer.

7. The recording material as claimed in claim 1, wherein the layer containing the leuco dye further contains an organic solvent.

8. The recording material as claimed in claim 1, wherein the layer containing the leuco dye further contains an organic solvent, the amount of said leuco dye ranging from 2 to 20 weight % based on the amount of the organic solvent.

9. The recording material as claimed in claim 1, wherein the leuco dye is contained in microcapsules which are dispersed in the layer provided on the support, said microcapsules further containing an organic solvent.

* * * * *